(12) United States Patent
Matsubara et al.

(10) Patent No.: US 8,680,301 B2
(45) Date of Patent: Mar. 25, 2014

(54) LIPASE ACTIVITY INHIBITORS CONTAINING HIGH-MOLECULAR WEIGHT POLYPHENOL FRACTIONS, TEA EXTRACTS, AND PROCESSES FOR PRODUCING THE SAME

(75) Inventors: Hitoshi Matsubara, Osaka (JP); Yoshiyuki Ishikura, Ibaraki (JP); Hiroaki Sasaki, Kyoto (JP); Keiichi Abe, Ikeda (JP); Sumio Asami, Ibaraki (JP); Masaaki Nakai, Minoo (JP); Aki Kusumoto, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1755 days.

(21) Appl. No.: 10/589,607

(22) PCT Filed: Feb. 17, 2005

(86) PCT No.: PCT/JP2005/002411
§ 371 (c)(1),
(2), (4) Date: Aug. 16, 2006

(87) PCT Pub. No.: WO2005/077384
PCT Pub. Date: Aug. 25, 2005

(65) Prior Publication Data
US 2007/0178175 A1     Aug. 2, 2007

(30) Foreign Application Priority Data
Feb. 17, 2004  (JP) ................................. 2004-40679

(51) Int. Cl.
*C07D 403/00*     (2006.01)
*C07D 311/62*     (2006.01)

(52) U.S. Cl.
CPC ............ *C07D 403/00* (2013.01); *C07D 311/62* (2013.01)
USPC ........................................................ 549/399

(58) Field of Classification Search
None
See application file for complete search history.

(56) References Cited

U.S. PATENT DOCUMENTS

| | | | |
|---|---|---|---|
| 4,495,210 A | 1/1985 | Green et al. | 426/422 |
| 6,294,190 B1 | 9/2001 | Nakahara et al. | |
| 6,627,232 B1 | 9/2003 | Hammerstone, Jr. et al. | 424/776 |
| 8,088,429 B2 * | 1/2012 | Takashima et al. | 426/597 |
| 2002/0146472 A1 | 10/2002 | Chen et al. | |
| 2004/0097432 A1 | 5/2004 | Roh-Schmidt et al. | |
| 2004/0220117 A1 | 11/2004 | Tagashira et al. | 514/27 |

FOREIGN PATENT DOCUMENTS

| | | |
|---|---|---|
| EP | 0 040 712 B2 | 4/1989 |
| JP | 1 45345 | 10/1989 |
| JP | HEI 3-219872 | 1/1990 |
| JP | HEI 4-182479 | 11/1990 |
| JP | 03-219872 A | 9/1991 |
| JP | 03-228664 A | 10/1991 |
| JP | 5017352 A | 1/1993 |
| JP | HEI 6-9607 | 1/1994 |
| JP | 08-070772 A | 3/1996 |
| JP | HEI 8-109178 | 4/1996 |
| JP | 9-291039 | 11/1997 |
| JP | 10-004919 | 1/1998 |
| JP | 2001-321166 | 11/2001 |
| JP | 2002-370980 | 12/2002 |
| JP | HEI 2003-146898 | 5/2003 |
| JP | HEI 2003-231684 | 8/2003 |
| JP | 08-070772 | 3/2006 |
| WO | WO 03/045328 | 6/2003 |

OTHER PUBLICATIONS

Nadine Taylor, The Green Tea Library, "Green, Black or Oolong?", also available at http://www.greentealibrary.com/Green,%20Black%20or%20Oolong%20-%20Article.htm; last viewed Aug. 9, 2011.*

Tewari, Sunita et al., Indian J. Physiol. Pharmacol., "Comparative Study of Antioxidant Potential of Tea With and Without Additives", 2000, vol. 44, No. 2, pp. 215-219.*

Chin et al., "Clinical Efficacy of Oolong Tea on Anti-Simple Obesity," Nihon Rinsho Eiyou Gakkai-shi (The Japanese Society of Clinical Nutrition Magazine) 20(1): 83-90, 1998 (translation).

"Suppressive Effect of Oolong Tea Polymerized Polyphenols-enriched Oolong Tea on Postprandial Serum Triglyceride Elevation," Jpn Pharmacol Ther, vol. 32, No. 6, pp. 335-342.

Hashimoto et al., "Evaluation of Tea Polyphenols as Anti-HIV Agents," Bioorganic & Medicinal Chemistry Letters, vol. 6, No. 6, (1996), pp. 695-700.

International Search Report issued on Aug. 16, 2005 in PCT/JP2005/012401 filed Jul. 5, 2005.

Hong et al., Effects of Tea Polyphenols on Arachidonic Acid Metabolism in Human Colon, Chapter 4 in Food Factors in Health Promotion and Disease Prevention, pp. 27-38, ACS Symposium Series, vol. 851, American Chemical Society, Jun. 19, 2003.

(Continued)

Primary Examiner — Eric S Olson
(74) Attorney, Agent, or Firm — Drinker Biddle & Reath LLP

(57) ABSTRACT

There are provided foods and beverages that will suppress the absorption of dietary lipids, thereby suppressing the rise of triglyceride in blood. High-molecular weight polyphenol fractions recovered from oolong tea are added to foods or beverages as an active ingredient for inhibiting lipase activity. The foods and beverages of the present invention are safe and their inherent flavor has not been impaired; hence, they may be taken in routinely so that the lipase inhibitory action of the high-molecular weight polyphenol fractions will suppress the rise of triglyceride in blood and prevent obesity.

9 Claims, 3 Drawing Sheets

(56) References Cited

OTHER PUBLICATIONS

Hashimoto et al., Evaluation of the Anti-oxidative Effect (in vitro) of Tea Polyphenols, Biosci. Biotechnol. Biochem., vol. 67, No. 2, pp. 396-401, Feb. 2003.

Kumazawa, Cha Seibun no Seitaimaku ni Taisura Shinwasei (1), Cha, 2001, vol. 54, No. 2, pp. 36-37 (in Japanese).

Office Action dated May 4, 2010 in U.S. Appl. No. 11/631,507, filed Jan. 4, 2007.

Office Action dated Aug. 3, 2009 in U.S. Appl. No. 11/631,507, filed Jan. 4, 2007.

Office Action dated Jun. 15, 2009 in U.S. Appl. No. 11/631,507, filed Jan. 4, 2007.

Hara et al., "Suppressive Effect of Oolong Tea Polymerized Polyphenols-enriched Oolong Tea on Postprandial Serum Triglyceride Elevation," *Jpn. Pharmacol. Ther.*, vol. 32, No. 6, pp. 335-342, 2004 (w/English-language translation).

Fukui et al., "Lipase inhibitory activity and Suppressive Effect on Serum Triglyceride Elevation of Oolong Tea Polymerized Polyphenols," *Himan Kenkyu* vol. 32, Supplement, p. 182, 2004 (w/ English-language translation).

Iwata, "Effects of Oolong Tea on Lipid Metabolism," *Joshi Eiyo Daigaku Kiyo* (*Journal of Kagawa Nutrition College*), Dec. 1996, vol. 27, pp. 11-21 (w/English-language translation).

Iwata et al., "Effect of Oolong Tea on Plasma Lipids and Lipoprotein Lipase Activity in Young Women," *Nihon Eiyou Shokuryou Gakkai-shi* (*Journal of Japanese Society of Nutrition and Food Science*), Aug. 10, 1991, vol. 44, No. 4, pp. 251-259 (w/ English-language translation).

Chin et al., "Clinical Efficacy of Oolong Tea on Anti-Simple Obesity," *Nihon Rinsho Eiyou Gakkai-shi* (*The Japanese Society of Clinical Nutrition Magazine*) 20(1): 83-90, 1998.

Ikeura et al., "Anti-adipogenic effect of cocoa—In vitro experiment of lipase inhibitory effect," *The Japanese Society of Nutrition and Food Science Sokai Koen Yoshishu*, p. 243 Apr. 1, 2003 (w/ English-language translation).

Iwata, "Effects of Oolong Tea on Lipid Metabolism," Joshi Eiyo Daigaku Kiyo, Dec. 1996, vol. 27, pp. 11-21.

Iwata et al., "Effect of Oolong Tea on Plasma Lipids and Lipoprotein Lipase Activity in Young Women," Journal of Japanese Society of Nutrition and Food Science, Aug. 10, 1991, vol. 44, No. 4, pp. 251-259 (English language translation of Abstract).

International Preliminary Report on Patentability dated Sep. 19, 2006, in International PCT Application No. PCT/JP2005/002411.

International Search Report dated Apr. 28, 2005, in PCT/JP2005/002411 (previously submitted).

"Suppressive Effect of Oolong Tea Polymerized Polyphenols-enriched Oolong Tea on Postprandial Serum Triglyceride Elevation," Jpn Pharmacol Ther, vol. 32, No. 6, pp. 335-342, (2004).

\* cited by examiner

Fig. 1
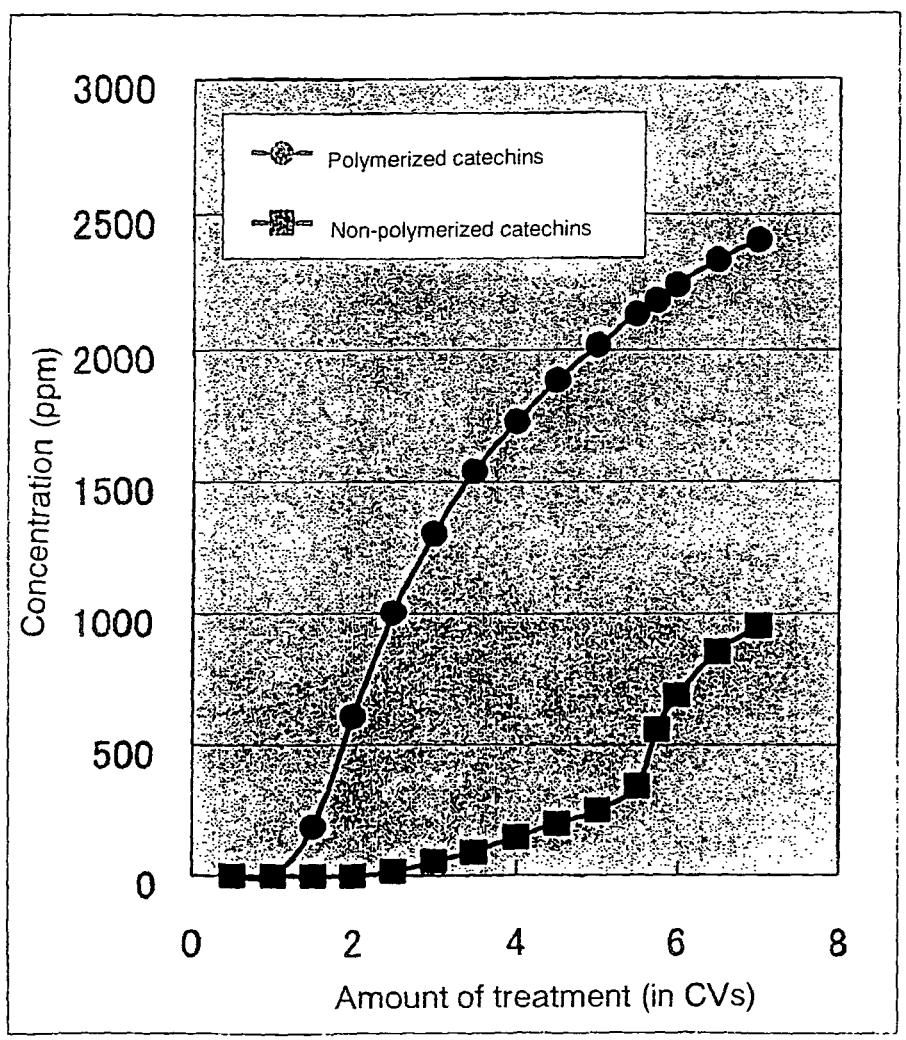
Fig. 2
Fig. 2-1
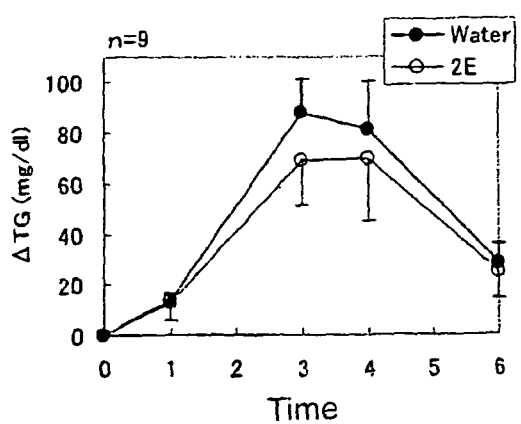
Fig. 2-2
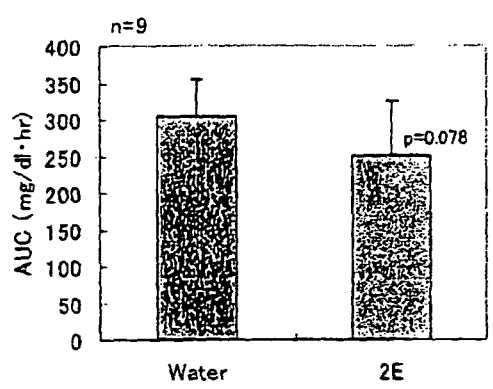

Fig.3
Fig. 3-1
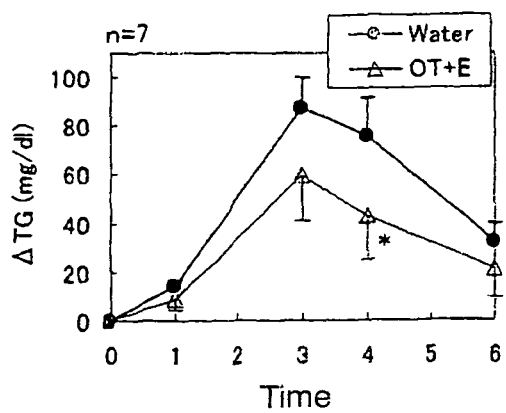
Fig. 3-2
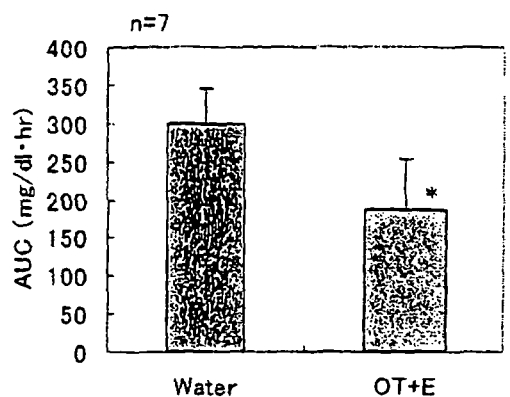
Fig.4
Fig. 4-1
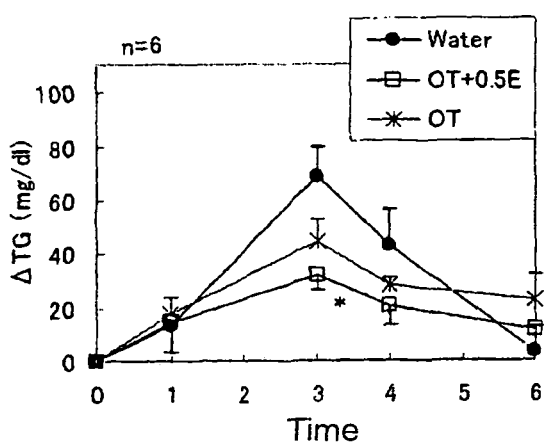
Fig. 4-2
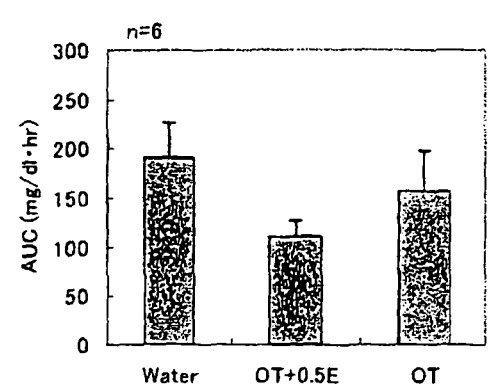

LIPASE ACTIVITY INHIBITORS CONTAINING HIGH-MOLECULAR WEIGHT POLYPHENOL FRACTIONS, TEA EXTRACTS, AND PROCESSES FOR PRODUCING THE SAME

TECHNICAL FIELD

The present invention has been accomplished on the basis of the finding that high-molecular weight polyphenols (polymerized catechins) contained in oolong tea and other tea products exhibit various beneficial effects whereas they are less astringent and bitter than other tannins and non-polymerized catechins. It relates to a method of selectively fractionating polymerized catechins in tea, etc., compositions such as tea extracts that are obtained by that method with the polymerized catechins in enriched form, lipase activity inhibitors containing the fractions obtained by that method, and foods or beverages that have the compositions added thereto and which are not impaired in flavor but present high preferences and can be taken in for health promoting purposes.

BACKGROUND ART

With the recent tendency toward westernized eating habits in Japan, intake of high fat diet continues to increase. According to a National Nutrition Survey in Japan (1999), it is reported that although their energy intake is decreasing every year, their fat energy ratio exceeds the reasonable proportion of 25%, and 50 to 60% of people over 60 are recognized to have high triglyceride and cholesterol values [A Summary of 1999 National Nutrition Survey in Japan by The Ministry of Health, Labor and Welfare, Rinsho Eiyo (Clinical nutrition) 2001; 98(5): 577-588].

Obesity is one of the most severe diseases in present day society, caused by excessive fat intake. The excessive fat intake causes not only obesity, but also disorders caused by obesity such as diabetes, hyperlipidemia, hypertension and arteriosclerosis. In Japan, Mazindole® as an anorectic drug is only one therapeutic drug with official approval for treating obesity. However, this drug is reported to have side effects such as excessive thirst (mouth dryness), constipation, epigastric distress, nausea and vomiting [Rinsyo Hyouka (Clinical evaluation), 1985; 13(2): 419-459, Clinical evaluation, 1985; 13(2): 461-515]. In overseas, Xenical® as a lipase inhibitor which suppresses fat absorption in the gastrointestinal tract, is on market as an obesity treatment drug. However, this drug is also reported to have side effects such as fatty stool, increased stool frequency, soft stool, diarrhea and stomachache. Therefore, using this drug is sometimes accompanied by concerns about safety (The Lancet 1998; 352:67-172).

To prevent obesity, it is advantageous to reduce the caloric intake by controlling diet. However, it requires careful guidance on nutrition making it difficult to practice in daily life. Therefore, inhibiting the absorption of dietary lipids in the body in a safe and healthy manner is practical and useful for treatment of obesity and related diseases and in promoting health.

With these facts in mind, the development of a "food for specified health uses" which is safe to use and is proven to be effective in treating humans is attracting a lot of attention. Food materials which inhibit increase of serum triglyceride after a meal, such as: a globin protein decomposition product that suppresses fat absorption by pancreatic lipase inhibitory activity [J. Nutr. 1988; 128: 56-60, Nihon Eiyou Shokuryou Gakkai-shi (Journal of Japanese society of Nutrition and Food Science) 1999; 52(2): 71-77, Kenkou Eiyou Shokuhin Kenkyu (Health food and nutrition food Research) 2002; 5(3): 131-144]; diacylglycerol with different digestion and absorption features compared to triacylglycerol (J. Am. Coll. Nutr. 2000; 19(6): 789-796, Clin. Chim. Acta. 2001; 11(2): 109-117); eicosapentaenoic acid (EPA) and docosahexanoic acid (DHA) purified from fish oil; are on market as foods for specified health use until now.

On the other hand, reports on lipid-improving effect of oolong tea are: significant decrease in blood triglyceride after drinking 1330 ml/day of commercial oolong tea for 6 weeks [Nihon Eiyou Shokuryou Gakkai-shi (Journal of Japanese society of Nutrition and food science) 1991; 44(4): 251-259]; and oral administration of oolong tea (2 g×4/day) for 6 consecutive weeks to 102 males and females with simple obesity resulted in more than 1 kg weight loss in 67% of the subjects and significant improvement in the subjects with high blood acylglycerol after taking oolong tea [Nihon Rinsho Eiyou Gakkai-shi (The Japanese Society of Clinical Nutrition Magazine) 1998; 20(1): 83-90]. These reports show that although drinking a large quantity of oolong tea is recognized to be effective, it is difficult in daily life to continue drinking such large quantities of a drink such as oolong tea. Further, simply providing concentrated oolong tea is not an appropriate and a practical option, due to its strong bitterness and astringency and increased caffeine content.

Speaking of high-molecular weight polyphenols (polymerized catechins) contained in oolong tea and other tea products, they exhibit various beneficial effects whereas they are less astringent and bitter than other tannins and non-polymerized catechins. It is therefore desired to establish an efficient method by which the catechins contained in oolong tea and other tea products can be separated into non-polymerized catechins and polymerized catechins.

It has been known that a variety of ingredients in tea can be separated by various resins. For instance, it has been known that detanning and decaffeination are possible by treating with activated charcoal. However, there has not been known any effective method that can selectively separate polymerized catechins from non-polymerized catechins by means of an adsorbent such as activated charcoal or an adsorbing resin.

Non-patent document 1: A Summary of 1999 National Nutrition Survey in Japan by the Ministry of Health, Labor and Welfare, 2001 98(5): 577-588

Non-patent document 2: Rinsho Hyouka (Clinical nutrition) 1985; 13(2): 419-459

Non-patent document 3: Rinsho Hyouka (Clinical nutrition) 1985; 13(2): 461-515

Non-patent document 4: The Lancet 1998; 352: 67-172

Non-patent document 5: J. Nutr. 1988; 128: 56-60, 1988

Non-patent document 6: Nihon Eiyou Shokuryou Gakkai-shi (Journal of Japanese Society of Nutrition and Food Science) 1999; 52(2): 71-77

Non-patent document 7: Kenkou Eiyou Shokuhin Kenkyu (Health food and nutrition food Research) 2002; 5(3): 131-144

Non-patent document 8: J. Am. Coll. Nutr. 2000; 19(6): 789-796

Non-patent document 9: Clin. Chim. Acta. 2001; 11(2): 109-117

Non-patent document 10: Nihon Eiyou Shokuryou Gakkai-shi (Journal of Japanese Society of Nutrition and food science) 1991; 44(4): 251-259

Non-patent document 11: Nihon Rinsho Eiyou Gakkai-shi (The Japanese Society of Clinical Nutrition Magazine) 1998; 20(1): 83-90

DISCLOSURE OF INVENTION

Problems to be Solved by the Invention

The present invention provides foods or beverages and lipase activity inhibitors that will suppress the absorption of dietary lipids, thereby suppressing the rise of triglyceride in blood, and/or prevent obesity.

The present invention provides a method by which a mixture of non-polymerized catechins and polymerized catechins, say, oolong tea is so treated as to separate the former from the latter or vice versa.

The present invention provides a method in which an aqueous liquid containing polymerized catechins and non-polymerized catechins is brought into contact with an adsorbent selected from the group consisting of activated charcoal and an adsorbent resin as the aqueous liquid is held at a temperature of at least 50° C., whereby the non-polymerized catechins are selectively removed so that the ratio of the polymerized catechins to the non-polymerized catechins is made higher than in the original aqueous liquid. The invention also provides an aqueous solution that has been produced by that method, or a composition comprising a concentrated or dried form of that aqueous solution.

The present invention also provides an oolong tea extract in which the ratio of the polymerized catechins to the non-polymerized catechins is made higher than in the ordinary oolong tea (liquid extract).

The present invention further provides a lipase activity inhibitor as well as a food or beverage additive that contain the composition or tea extract.

Means for Solving the Problem

DEFINITIONS

The term "polymerized catechins" as used herein has the same meaning as high-molecular weight polyphenols contained in teas and they refer to those tea catechins which have been polymerized into dimers or higher polymers, as contrasted with non-polymerized catechins. Tea catechins is the collective name for catechins contained in teas, and catechins derived from other naturally occurring materials or even synthetic catechins are covered by the definition of tea catechins herein as long as they are catechins contained in teas.

Non-polymerized catechins are tea catechins in monomeric form. The eight major non-polymerized catechins in oolong tea are catechin, gallocatechin, catechin gallate (CG), gallocatechin gallate (GCG), epicatechin, epigallocatechin, epicatechin gallate (ECG), and epigallocatechin gallate (EGCG).

The high-molecular weight polyphenol fraction as used herein refers to an oolong tea extract that is obtained by a process in which an aqueous liquid extract from a material such as oolong tea that contains polymerized catechins and non-polymerized catechins in admixture, and has the polymerized catechins selectively enriched so that the ratio of the polymerized catechins to the non-polymerized catechins is made higher than in the oolong tea's liquid extract (aqueous liquid extract).

The adsorbed catechins as used herein means tea catechins that are adsorbed on an adsorbent when the method of the present invention (say, the method adopted in Example 2 at a temperature of 60° C.) is implemented, and most of them are non-polymerized catechins. It should be apparent to those skilled in the art that a small portion of polymerized catechins are also adsorbed on the adsorbent. The non-adsorbed catechins means tea catechins that are not adsorbed on the said adsorbent, and most of them are polymerized catechins. It should be apparent to those skilled in the art that a small portion of non-polymerized catechins are also contained in the non-adsorbed catechins.

(1) The Invention of the Lipase Activity Inhibitor

The present inventors found that an ingredient in oolong tea that inhibits lipase, in particular, pancreatic lipase, which is essential to the absorption of lipids was present in the polyphenol fraction of oolong tea that was recovered as a non-adsorbed fraction by subjecting oolong tea to a column of adsorbent such as activated charcoal and which contained little or no part of caffeine and non-polymerized catechins. The present invention has been accomplished on the basis of this finding and it relates to a lipase activity inhibitor that comprises, as an active ingredient for suppressing the absorption of lipids to thereby suppress the rise of triglyceride in blood and/or for preventing obesity, a high-molecular weight polyphenol fraction isolated from oolong tea, as well as a food or beverage that contains the said high-molecular weight polyphenol fraction.

The high-molecular weight polyphenol fraction isolated from oolong tea which is to be used in the present invention is characterized in that the amount of polymerized catechin (high-molecular weight polyphenol) relative to non-polymerized catechin is at least four times as much. The method of obtaining the high-molecular weight polyphenol fraction is part of the present invention and will be described later.

The lipase inhibiting active ingredient of the present invention contains little or no part of the non-polymerized catechins, so it does not very much feel bitter or astringent; in addition, it does not contain caffeine, so it may be added in any desired amount to foods or beverages without impairing their flavor and the foods or beverages that contain it may be ingested in large amounts without causing excessive intake of caffeine. As a further advantage, the lipase inhibiting active ingredient of the present invention derives form oolong tea and is highly safe. Hence, the food or beverage of the present invention may be ingested every day or routinely in order to exhibit the intended efficacy in a consistent manner. Therefore, the amount in which the high-molecular weight polyphenol fraction is added to the food or beverage substantially has no upper or lower limit. However, in order to achieve the effect of lipase inhibiting activity, the fraction may be added to the food or beverage in such an amount that at least 67 mg of the polymerized catechins can be taken in per serving (say, about 250 ml). In this case, the amount of the polymerized catechins contained in the food or beverage after the fraction is added can be measured by the high-performance liquid chromatography shown in Example 1, namely by performing gradient elution on a reverse-phase column with the recovered polymerized catechins used as the standard substance.

The high-molecular weight polyphenol fraction of oolong tea may be added to various foods or beverages as the ingredient of lipase inhibiting activity. Examples of beverages include liquid tonics, health drinks, nutritional supplement drinks, sports drinks, etc. Examples of foods include health foods and nutritional supplement foods.

The lipase activity inhibitor of the present invention is such that the high-molecular weight polyphenol fraction isolated from oolong tea is either a liquid fraction or a concentrated or dried form thereof, the liquid fraction being obtained by a process in which an aqueous extract of oolong tea is brought into contact with an adsorbent selected from the group consisting of activated charcoal and an adsorbent resin, whereby non-polymerized catechins are selectively removed to enhance the ratio of polymerized catechins to the non-polymerized catechins.

(2) The Invention of the Process for Producing the Tea-Derived High-Molecular Weight Polyphenol Fraction The present inventors conducted intensive studies on the method of separating non-polymerized catechins from polymerized catechins and found a method in which an adsorbent is used at a controlled temperature of 50° C. or more, whereby polymerized catechins are selectively enriched to yield the high-molecular weight polyphenol fraction (the composition or tea extract in which the ratio of the polymerized catechins to the non-polymerized catechins is increased).

Therefore, the method of the present invention is characterized in that an aqueous liquid containing polymerized catechins and non-polymerized catechins is brought into contact with an adsorbent selected from the group consisting of activated charcoal and an adsorbent resin as the aqueous liquid is held at a temperature of at least 50° C., whereby the non-polymerized catechins are selectively removed so that the ratio of the polymerized catechins to the non-polymerized catechins is made higher than in the original aqueous liquid.

Temperature

Setting the temperature at 50° C. or higher is an essential condition for the present invention to ensure that non-polymerized catechins are selectively adsorbed on the adsorbent so that non-polymerized catechins are removed; at lower temperatures, say, room temperature, it is impossible to selectively separate the polymerized catechins from the non-polymerized catechins. The temperature has no particular upper limit and any temperature up to the boiling point may be employed to implement the present invention. If desired, temperatures exceeding 100° C. may be employed under super-atmospheric pressure.

Starting Material

The aqueous liquid containing the polymerized catechins and non-polymerized catechins is not limited in any particular way but the method of the present invention is useful for efficiently separating the polymerized catechins from the non-polymerized catechins typically in liquid extracts of plants such as tea, in particular, oolong tea. The following explanation refers to oolong tea but this is not the sole example of the present invention.

Pretreatments

The starting material containing polymerized catechins and non-polymerized catechins, for example, leaves of oolong tea are optionally shredded and then extracted appropriately with water. The temperature of the water used for extraction is not limited to any particular value; however, in order to improve the extraction efficiency by shortening the extraction time, the temperature is preferably 50-99° C., more preferably 80-99° C. In order to render the liquid extract slightly alkaline, sodium hydrogencarbonate may be added to it before use. Sodium hydrogencarbonate may be added at any concentration from zero up to saturation. For example, sodium hydrogencarbonate may be added in an amount of 1.0-2.0 g per liter of warm water; alternatively, it may be added in an amount that gives a pH of 8.0-8.5, preferably about 8.2. Sodium hydrogencarbonate may be replaced by other weakly basic substances of high safety. After the extraction step, settling, centrifugation and/or filtration may be performed in order to remove the solids; if desired, vitamin C (VC) may be added.

The concentration of the liquid extract of oolong tea which is to be brought into contact with the adsorbent is 2.0-6.0, preferably about 3.7, in terms of Brix.

Adsorbent

For separation, an adsorbent selected from the group consisting of activated charcoal and an adsorbent resin is employed. The adsorbent may conveniently be used in a column and the selection of a suitable particle size for the adsorbent to be used in column treatment is also an important factor to consider. In order to reduce the pressure loss from the use of a column, a large particle size is preferred, but on the other hand, in order to ensure that the adsorbent has a sufficient adsorptive surface to perform efficient separation, a smaller particle size is preferred. Depending on the adsorbent to be used, an optimum particle size can be selected by skilled artisans within the scope of their routine technical knowledge. If the adsorbent is particulate activated charcoal, the one shown in the Examples with a size of 32 mesh to 60 mesh is particularly preferred.

The particulate activated charcoal may be replaced by a synthetic adsorbent resin, for example, one that is prepared from polystyrene. In this case, too, the pore size is an important factor to consider and the appropriate resin must be chosen to ensure effective separation. Commercial products that may be advantageously used include SEPABEADS SP825 and SP850 manufactured by Mitsubishi Chemical Corporation that have average pore sizes of 57.4 angstrom and 38.1 angstrom, respectively.

The Amount in which the Adsorbent is to be Used

In order to perform the method of the present invention efficiently, the adsorbent is desirably used in a larger amount. If the method is to be performed on a column, its effectiveness is increased by causing the liquid extract of oolong tea to flow through the column for separation in a smaller quantity and its quantity is preferably from five times (5 CV) to ten times (10 CV) the capacity of the column. The requirement that the adsorbent be used in an amount not smaller than a certain value with respect to the quantity of the liquid extract of oolong tea is as important for the present invention as the requirement that the temperature for adsorption treatment be held at 50° C. or higher.

In short, it has conventionally been assumed that neither the polymerized catechins nor the non-polymerized catechins are sufficiently adsorbed on the adsorbent; however, according to the present invention, it has been found that the non-polymerized catechins can be selectively adsorbed in a sufficient way by holding the temperature for adsorption treatment at 50° C. or above and using a sufficient amount of the adsorbent.

Time of Contact with the Adsorbent

The time over which the liquid extract of oolong tea (aqueous liquid extract) is held in contact with the adsorbent is not limited to any particular value as long as it is sufficient for the non-polymerized catechins to be adsorbed on the adsorbent. If adsorption is to be performed on a column, a guide figure for the flow rate is SV=1-6, preferably about 3.

Post-Treatment

The extract of oolong tea (the high-molecular weight polyphenol fraction, composition, or tea extract) that has been separated from the adsorbent may be directly used as a beverage abundant in the high-molecular weight polyphenol (polymerized catechins); alternatively, it may be used as a material for foods and beverages or for pharmaceuticals. If necessary, it may be exposed to heat, placed under reduced pressure, freeze-dried or otherwise treated so that it can be used in a concentrated or dried form.

(3) The High-Molecular Weight Polyphenol Fraction Derived from the Production Process The present invention relates to an aqueous, wet or dry composition that has been produced by the above-described method of the present invention to have an enhanced ratio of the polymerized catechins to the non-polymerized catechins. The composition of the present invention is a tea extract, preferably an oolong tea extract. In the composition (tea extract), the ratio of polymerized catechin relative to non-polymerized catechin is preferably at least four.

The proportion of polymerized catechin relative to non-polymerized catechin can be confirmed by measurement that is conducted by the method used in Example 1 that will be described later.

Effects of the Invention

Commercial products of oolong tea are not very effective in suppressing the postprandial rise in triglyceride and if their concentration is simply increased, the bitterness and astringency, as well as the caffeine content are also increased, making them unsuitable for drinking. In the present invention, the high-molecular weight polyphenol fraction that is contained in oolong tea and which is abundant in the polymerized catechins is isolated and added to foods or beverages; this is expected to provide effectiveness in suppressing the rise of triglyceride without impairing the flavor of the food or beverage to which the high-molecular weight polyphenol fraction has been added, and prevention of obesity is realized. In order to suppress the absorption of dietary fat, such food or beverage is desirably taken in together with a meal and beverages enriched in the tea-derived active ingredient have great significance.

The present invention offers another advantage in that it enables selective separation of the polymerized catechins from the non-polymerized catechins to be performed by easy operation although this has heretofore been held difficult to achieve.

BRIEF DESCRIPTION OF THE DRAWINGS

FIG. 1 is a graph showing an exemplary behavior of the two ingredients in a liquid extract of oolong tea that was subjected to a separation step at 60° C.

FIG. 2-1 is a graph showing how the change (ΔTG) in the triglyceride level in blood after fat loading of an animal group that drank an aqueous solution (2E) of the polyphenol fraction of oolong tea varied over time, as compared with a group that drank pure water. FIG. 2-2 shows the areas under curve (AUC) of the graph shown in FIG. 2-1.

FIG. 3-1 is a graph showing how the change (ΔTG) in the triglyceride level in blood after fat loading of an animal group that drank an aqueous solution (OT+E) of polyphenol-enriched oolong tea varied over time, as compared with a group that drank pure water. FIG. 3-2 shows the areas under curve (AUC) of the graph shown in FIG. 3-1.

FIG. 4-1 is a graph showing how the change (ΔTG) in the triglyceride level in blood after fat loading of an animal group that drank oolong tea (OT) and a group that drank polyphenol-enriched oolong tea (OT+0.5E) varied over time, as compared with a group that drank pure water. FIG. 4-2 shows the areas under curve (AUC) of the graph shown in FIG. 4-1.

EXAMPLE 1

Figure 5:
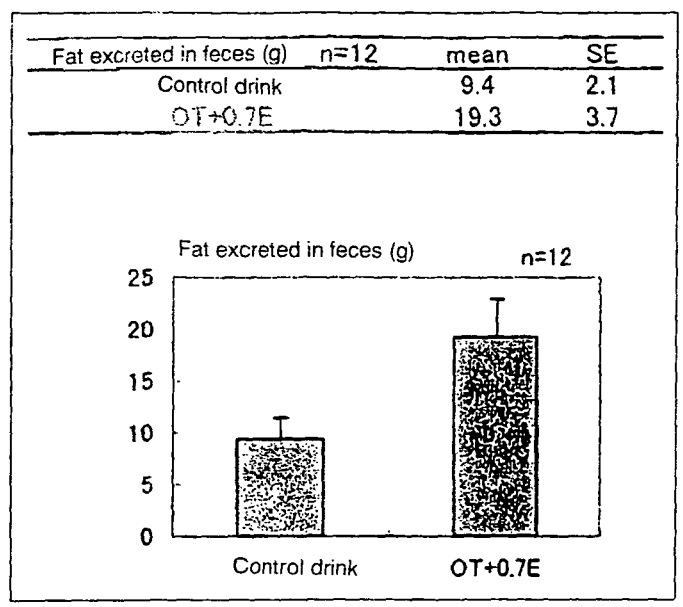
FIG. 5 shows the fat excretion promoting action of polyphenol-enriched oolong tea.

Extraction of Tea Leaves (1) The efficiency of extracting the solids in oolong tea was compared between two cases; in one case, sodium hydrogencarbonate (1.67 g) was dissolved in 1 L of warm water (90° C.) to give a pH of 8.22, and in the other case, no sodium hydrogencarbonate was added and the resulting pH was 6.79. In each case, 100 g of oolong tea leaves were added to 1 L of warm water and the mixture was gently agitated for 20 minutes to effect extraction at a controlled temperature of 90° C.

The liquid extract in each case was measured for Brix concentration and pH. In the absence of sodium hydrogencarbonate, Brix 3.76 and pH 5.06 were recorded; in the presence of sodium hydrogencarbonate, the respective values were 4.27 and 6.15. Using sodium hydrogencarbonate, one could obtain an apparently dark liquid extract and this improvement in the extraction of the solids was also confirmed by the Brix value.

(2) Sodium hydrogencarbonate (1.67 g) was dissolved in 1 L of warm water at 90° C. and 100 g of oolong tea leaves were then added. The mixture was gently agitated for 5 minutes to effect extraction at a controlled temperature of 90° C. After the extraction, a 140-mesh screen was used to separate the tea leaves from the liquid extract, which was centrifuged to remove the fine solids. In the remaining liquid, 1.59 g of VC was dissolved to make a liquid extract of oolong tea having a Brix value of 3.7.

(3) As a means of measuring the amounts of polymerized catechins and non-polymerized catechins, the column of Develosil C30 UG-3 (3 mmφ×15 cm; Nomura Chemical Co., Ltd.) was used under the following conditions: mobile phase A=0.1% HCOOH/$H_2O$; B=90% $CH_3CN$, 0.1% HCOOH/$H_2O$; 0.2 ml/min; gradient=B 10%→70% (15 min), B 70% iso (10 min); detection=A 280 nm.

The standard substance was polymerized catechin fractions that were repeatedly recovered from the liquid extract of oolong tea using a preparative ODS column.

The ingredients of the liquid extract are shown in Table 1.

TABLE 1

| Polymerized catechins: | 2235 ppm |
|---|---|
| Non-polymerized catechins*: | 3813 ppm |

*Non-polymerized catechins: the sum of catechin, gallocatechin, catechin gallate (CG), gallocatechin gallate (GCG), epicatechin, epigallocatechin, epicatechin gallate (ECG), and epigallocatechin gallate (EGCG)

EXAMPLE 2

Separation

Fifty milliliters of commercial particulate activated charcoal (e.g., GW-H32/60 of KURARAY CO., LTD.) was degassed and packed into a column. The liquid extract of oolong tea obtained in Example 1 was passed through the column at a flow rate of SV=3 to separate the ingredients. For this operation, the temperature of the liquid extract and the column was set at 20, 40, 50 or 60° C.; the results of analysis of the separated ingredients following a separation for about 5 CV at each temperature are shown in Table 2.

TABLE 2

| Polymerized catechins | | Non-polymerized catechins |
|---|---|---|
| Liquid extract | 2235 ppm | 3813 ppm |
| 20° C. | 1592 | 1094 |
| 40° C. | 1532 | 685 |
| 50° C. | 1470 | 351 |
| 60° C. | 1526 | 267 |

Thus, it was found that the higher the temperature for separation, the more selectively the non-polymerized catechins could be separated for removal.

FIG. 1 shows an exemplary behavior of the two ingredients when they were separated at 60° C.

EXAMPLE 3

Pilot Production

Leaves of oolong tea (600 kg) were subjected to column extraction with a 0.15% solution of sodium hydrogencarbonate (95° C.), whereupon a liquid extract was obtained in an amount of about 6,000 kg. With its temperature held at 60-65° C., the liquid extract was passed through a column of 400 kg particulate activated charcoal (GW-H32/60 of KURARAY CO., LTD.) so that non-polymerized catechins and caffeine were selectively removed. The effluent from the column was concentrated under reduced pressure to prepare about 900 kg of a tea extract having a Brix value of 10 or more.

The concentration of the polymerized catechins (OTPP) in the prepared tea extract was 14648 ppm, whereas that of the adsorbed catechins (EGCG+GCG+ECG+CG) was 366 ppm.

EXAMPLE 4

Lipase Inhibitory Activity

The liquid extract of Example 1 and the tea extract obtained in Example 3 which had the polymerized catechins enriched selectively (the non-polymerized catechins removed selectively) were compared for their action in inhibiting lipase which was known to be involved in fat absorption.

Lipase Inhibitory Activity Measurement:

Lipase activity measurement was carried out by using oleic acid ester of fluorescent 4-methylumbelliferone (4-UMO) as a substrate, and measuring the fluorescence of 4-methylumbelliferone produced by reaction.

In the measurement, 13 mM Tris-HCl containing 150 mM NaCl and 1.36 mM $CaCl_2$ was used as a buffer (pH 8.0). Substrate 4-UMO (Sigma) was prepared as 0.1M solution in DMSO and diluted 1000-fold with the buffer mentioned above. Similarly, lipase (porcine pancreatic lipase (Sigma)) was prepared as 400 U/ml solution in the buffer mentioned above and used in enzymatic measurement.

50 µl of the 4-UMO buffer solution and 25 µl of distilled water (or sample solution) were placed in a 96-well microplate and mixed at 25° C., followed by adding 25 µl of the lipase buffer solution to start enzyme reaction. After 30 minutes of reaction, 100 µl of 0.1M citric acid buffer (pH 4.2) was added to terminate the reaction, and the fluorescence of 4-methylumbelliferone (excitation wavelength: 355 nm, fluorescence wavelength: 460 nm) produced by the reaction was measured with a fluorescence plate reader (Labsystems, Fluoroskan Asent CF).

An inhibitory activity of the sample was determined as $IC_{50}$ (µg/ml), the amount of the sample which gave 50% of inhibition compared to the activity of control (distilled water).

The results are summarized in Table 3.

TABLE 3

|  | Lipase inhibitory activity ($IC_{50}$, mcg/ml) |
|---|---|
| Liquid extract | 0.97 |
| Tea extract | 0.62 |

EXAMPLE 5

Evaluation of Taste

The liquid extract of Example 1 and the tea extract obtained in Example 3 were each conditioned with distilled water to have a Brix value of 0.5; the thus prepared drinks were subjected to an organoleptic test on taste by 11 panelists. The results are summarized in Table 4.

TABLE 4

|  | Liquid extract | Tea extract |
|---|---|---|
| Too bitter and astringent to drink | 9 | 0 |
| Bitter and astringent but could be drunk | 2 | 4 |
| Bitter and astringent but by no means objectionable | 0 | 7 |

These results confirmed that the tea extract secured the intended efficacy and yet it was suppressed in bitterness and astringency.

EXAMPLE 6

Studying the Mixing Proportion Indexed by the Lipase Inhibitory Action

Lipase activity measurement for the high-molecular weight polyphenol fractions produced in the preparation example was carried out by using oleic acid ester of fluorescent 4-methylumbelliferone (4-UMO) as a substrate, and measuring the fluorescence of 4-methylumbelliferone produced by reaction.

In the measurement, 13 mM Tris-HCl containing 150 mM NaCl and 1.36 mM $CaCl_2$ was used as a buffer (pH 8.0). Substrate 4-UMO (Sigma) was prepared as 0.1M solution in DMSO and diluted 1000-fold with the buffer mentioned above. Similarly, lipase (porcine pancreatic lipase (Sigma)) was prepared as 400 U/ml solution in the buffer mentioned above and used in enzymatic measurement.

50 µl of the 4-UMO buffer solution and 25 µl of distilled water (or sample solution) were placed in a 96-well microplate and mixed at 25° C., followed by adding 25 µl of the lipase buffer solution to start enzyme reaction. After 30 minutes of reaction, 100 µl of 0.1M citric acid buffer (pH 4.2) was added to terminate the reaction, and the fluorescence of 4-methylumbelliferone (excitation wavelength: 355 nm, fluorescence wavelength: 460 nm) produced by the reaction was measured with a fluorescence plate reader (Labsystems, Fluoroskan Asent CF).

An inhibitory activity of the sample was determined as $IC_{50}$ (µg/ml), the amount of the sample which gave 50% of inhibition compared to the activity of control (distilled water). The reciprocal of $IC_{50}$ was calculated as the value of relative activity (in units) per µg and comparison was made for the strength of lipase inhibitory activity in sample solutions.

The drinks were prepared using oolong tea (OT; Brix 0.275) as base; a sample twice the concentration of OT was designated 2OT (Brix 0.55); to the base oolong tea (OT; Brix 0.275), the tea extract (E) obtained in Example 3 was added to provide a Brix value of 0.55 and the sample thus prepared was designated OT+E; a sample prepared in the same manner except that a tea extract half the concentration of E was added was designated OT+0.5E. The oolong tea used as the base was obtained by subjecting leaves of oolong tea to extraction with hot water.

TABLE 5

| Drink | units/ml |
|---|---|
| OT | $2.83 \times 10^3$ |
| OT + 0.5E | $5.04 \times 10^3$ |
| OT + E | $7.26 \times 10^3$ |
| 2OT | $5.67 \times 10^3$ |

EXAMPLE 7

Evaluation of Taste (for Drinks)

Polyphenol-enriched oolong tea (OT+E and OT+0.5E) and oolong tea (2OT) whose concentration was twice the ordinary value were each subjected to an organoleptic test on taste by 24 panelists. The results are summarized in the following table.

TABLE 6

|  | OT + 0.5E | OT + E | 2OT Tea |
|---|---|---|---|
| Too bitter and astringent to drink | 2 | 2 | 19 |
| Bitter and astringent but could be drunk | 7 | 11 | 5 |
| Bitter and astringent but by no means objectionable | 15 | 11 | 0 |

These results showed that by adjusting the mixing ratio (the weight ratio in terms of the solids content) of oolong tea (OT) to the tea extract (E) to be within the range between at least 1:1 and 2:1, it was possible to prepare drinks that secured the intended efficacy and which yet were suppressed in bitterness and astringency.

EXAMPLE 8

Tests for Evaluating the Efficacy of Drinks on Humans (to Verify the Effect of Reducing Postprandial Triglyceride)

Tests were conducted by a crossover design on healthy adults, both male and female. In each test, one cycle consisted of seven days, six of which were assigned to a washout period and a fat loading test was performed on the seventh day. Test 1 was performed with an aqueous solution (2E) of the polyphenol fraction of oolong tea; test 2 was performed with polyphenol enriched oolong tea (OT+E); and test 3 was performed with oolong tea (OT) and polyphenol enriched oolong tea (OT+0.5E). Each sample was used at a dose of 245 ml. The fat laden diet consisted of two ice creams and 1.5 egg rolls so that each volunteer would take in 40 g of fat. At various hours (0, 1, 3, 4, and 6) after the fat laden diet was ingested, a blood sample was collected from the vein of the forearm and comparison was made to see how the change in blood triglyceride level (ΔTG) after fat loading varied over time and how its area under curve (AUC) was affected; the drinks 2E, OT+0.5E and OT+E were confirmed to be capable of suppressing the rise in blood triglyceride level after fat loading. These results showed that the polymerized catechins proved effective when they were enriched to 360 mg/L (OT+0.5E) or more.

The results are shown in FIGS. 2, 3 and 4.

EXAMPLE 9

Tests for Evaluating the Efficacy of Drinks on Humans (to Verify the Fat Excretion Promoting Effect)

Tests were conducted by a crossover design on 12 healthy adults, both male and female. The drink under test was polyphenol enriched oolong tea (OT+0.7E) and the control drink was water that was colored with caramel and to which a flavor was added. In each test, the volunteers ingested the sample drink under test for ten consecutive days and the total amount of fat excreted in feces on the last three days was compared. The washout period consisted of seven days. As a result, the polyphenol enriched oolong tea was verified to have a significant fat excretion promoting action.

The results are shown in FIG. 5.

INDUSTRIAL APPLICABILITY

The composition or tea extract of the present invention is cleared of non-polymerized catechins, so their bitterness and astringency are significantly less than before the non-polymerized catechins were removed. In addition, they are sufficiently decaffeinated by treatment with an adsorbent. Therefore, they can be added to tea products (tea extracts) such as oolong tea and green tea to improve their taste.

According to the present invention, it was further found that the lipase activity inhibitor, composition or tea extract of the present invention have a significant lipase inhibitory activity. Hence, they can be used as additives that will be added to foods or beverages that may be oolong tea so that they will suppress the absorption of dietary lipids, thereby suppressing the rise of triglyceride in blood, and/or prevent obesity. Since the composition or tea extract of the present invention are substances that derive from nature, they are highly safe and can be ingested regularly (say, on every two or more days, every day, or after each meal) for an extended period of time to exhibit the intended effect.

The present invention also relates to a pharmaceutical for suppressing the absorption of dietary lipids to thereby suppress the rise of triglyceride in blood, and/or preventing obesity that contains the composition or tea extract of the present invention as an active ingredient for inhibiting lipase. The pharmaceutical is preferably shaped into a dosage form suitable for oral administration as exemplified by powder, granule, or tablet, pill, capsule, troche, candy, or chocolate, each of which may be administered as such or drunk after being dissolved in water. The amount of the composition or tea extract of the present invention in the pharmaceutical may range from 67 to 5,000 mg as polymerized catechins in one serving.

The invention claimed is:

1. A method of producing a composition comprising:
   extracting tea to obtain an aqueous liquid containing polymerized catechins and no-polymerized catechins, and
   contacting the aqueous liquid with an activated charcoal at a temperature of at least 50° C. to selectively remove the non-polymerized catechins to obtain the composition,
   wherein the composition has a higher ratio of the polymerized catechins to the non-polymerized catechins than that of the aqueous liquid.

2. A method of producing a composition
   extracting tea to obtain an aqueous liquid containing polymerized catechins and no-polymerized catechins,
   filling a column with an activated charcoal,
   passing the aqueous liquid through the column in an amount at least 3 times greater than the capacity of the column at a temperature of at least 50° C. to selectively remove the non-polymerized catechins,
   recovering an effluent from the column, and
   optionally concentrating or drying the effluent to obtain the composition having a higher ratio of the polymerized catechins to the non-polymerized catechins than that of the aqueous liquid.

3. A method of producing a beverage comprising:
extracting tea to obtain an aqueous liquid containing polymerized catechins and no-polymerized catechins,
contacting the aqueous liquid with an activated charcoal at a temperature of at least 50° C. to obtain an effluent, wherein the non-polymerized catechins are selectively removed; and
adding the obtained effluent to a base beverage to obtain the beverage.

4. The method of claim 3, wherein the base beverage is oolong tea.

5. The method of claim 2, wherein the amount of aqueous liquid passed is an amount of 5-10 times the capacity of the column.

6. The method of claim 2, wherein the aqueous liquid is obtained from slightly alkaline lukewarm water.

7. The method of any one of claims 1-2 and 5-6, wherein the tea is oolong tea.

8. The method of claim 3, wherein the tea is oolong tea.

9. The method of any one of claims 1-3, further comprising adding vitamin C to the aqueous liquid after the extraction step.

\* \* \* \* \*